Figure 1:
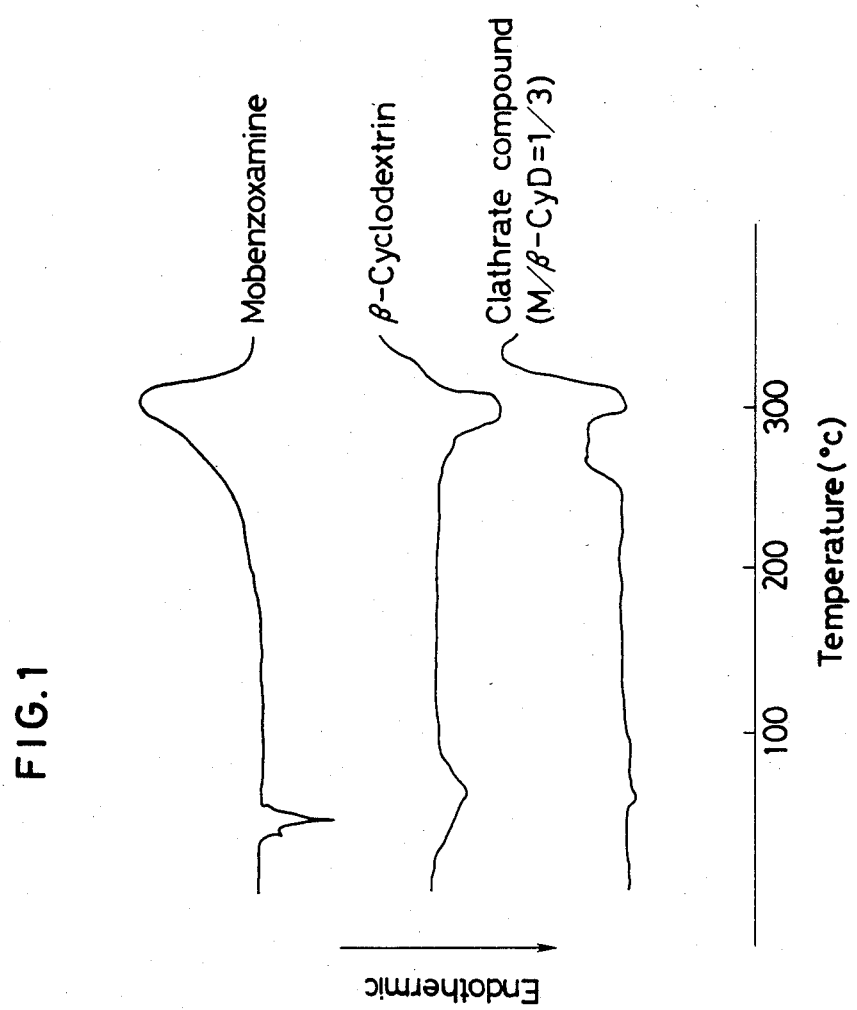

United States Patent [19]

Hasegawa et al.

[11] Patent Number: 4,608,366

[45] Date of Patent: Aug. 26, 1986

[54] ORAL CYCLODEXTRIN AND MOBENZOXAMINE PREPARATION

[75] Inventors: Takahito Hasegawa; Hideo Adachi, both of Takayama, Japan

[73] Assignee: Taiyo Pharmaceutical Industry Co., Ltd., Takayama, Japan

[21] Appl. No.: 739,275

[22] Filed: May 30, 1985

[30] Foreign Application Priority Data

Mar. 11, 1985 [JP] Japan ................................. 60-47642

[51] Int. Cl.⁴ ............................................. A61K 31/73
[52] U.S. Cl. ....................................... 514/58; 536/46; 536/103
[58] Field of Search ..................... 514/58; 536/103, 46

[56] References Cited

U.S. PATENT DOCUMENTS 4,438,106  3/1984  Wagu et al. ........................ 536/103
4,497,803  2/1985  Harada et al. ..................... 536/103

Primary Examiner—Johnnie R. Brown
Assistant Examiner—Elli Peselev
Attorney, Agent, or Firm—Oblon, Fisher, Spivak, McClelland & Maier

[57] ABSTRACT

Disclosed herein is an oral mobenzoxamine preparation which comprises a clathrate compound of mobenzoxamine or a salt thereof and cyclodextrin. Since the clathrate compound remains extremely stable even when stored for a long period of time and its absorption through the digestive tract is good upon its oral administration, the clathrate compound can be used advantageously as an orally-dosable preparation.

1 Claim, 2 Drawing Figures

ORAL CYCLODEXTRIN AND MOBENZOXAMINE PREPARATION

This invention relates to an oral mobenzoxamine preparation, and more specifically to an oral mobenzoxamine containing mobenzoxamine as a clathrate compound with cyclodextrin and having excellent absorbability through the digestive tract and superb stability.

1-[2-(4-Methoxybenzhydryloxy)ethyl]-4-[3-(4-fluorobenzoyl)propyl]piperazine (mobenzoxamine) has excellent antiemetic and antispasmodic activities (see, U.K. Pat. No. 1,529,782) and researches are now under way on its clinical applications.

Mobenzoxamine and its salts are however accompanied by such drawbacks that they are unstable and when stored for long periods of time, their activities are significantly reduced, and although they can give high concentrations in blood upon their pareneral administration such as their injection or the like, their absorption through the digestive tract are poor and they cannot thus give high concentrations in blood upon their oral administration. Accordingly, their formation into dosable preparations were difficult.

Under the above-described circumstances, the present inventors conducted an extensive research with a view toward solving the above-described problems. As a result, it has been found that when mobenzoxamine or a salt thereof is converted to a clathrate compound with cyclodextrin, it remains stable even when stored for a long period of time and moreover, its absorption through the digestive tract is good, leading to a high concentration in blood. The present invention has been completed on the basis of the above finding.

In one aspect of this invention, there is thus provided an oral mobenzoxamine preparation which comprises a clathrate compound of mobenzoxamine or a salt thereof and cyclodextrin.

Since the above-described clathrate compound between mobenzoxamine or its salt and cyclodextrin, which pertains to the present invention, remains extremely stable even when stored for a long period of time and its absorption through the digestive tract is good upon its oral administration, the clathrate compound can be used advantageously as an orally-dosable preparation.

The clathrate compound of this invention can be formed, either singly or together with a suitable excipient or the like, into powder, tablets, granules, capsules and so on.

Figure 2:
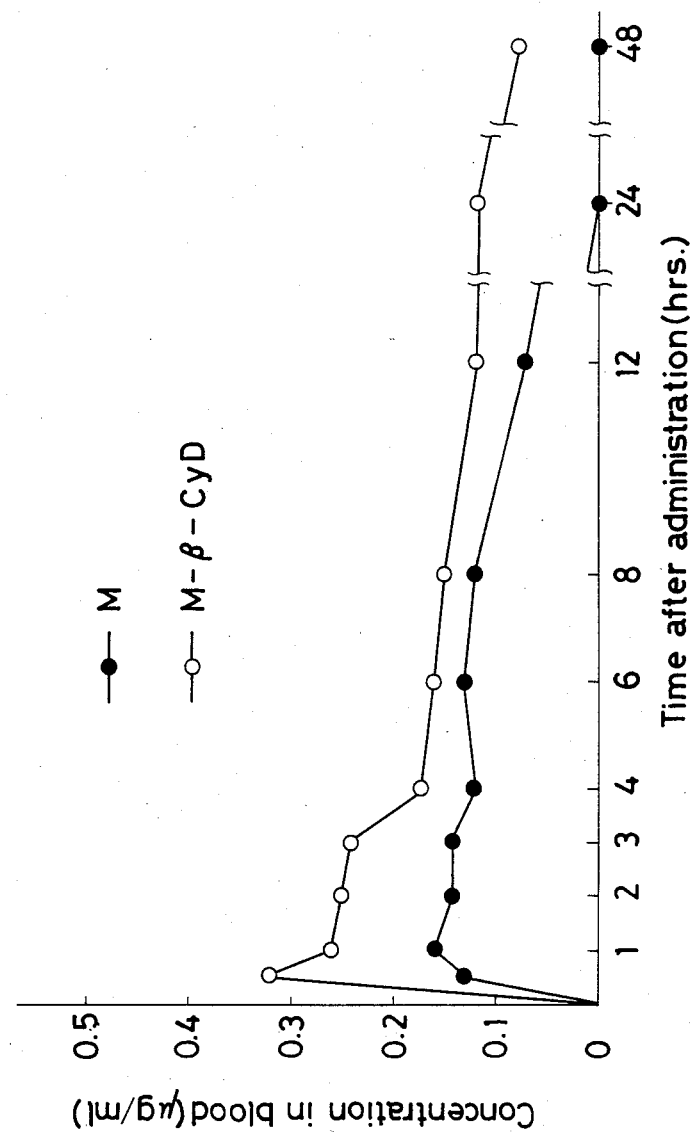

The above and other objects, features and advantages of the present invention will become apparent from the following description and the appended claims, taken in conjunction with the accompanying drawings, in which:

FIG. 1 is a differential thermal analysis diagram of mobenzoxamine, $\beta$-cyclodextrin and the clathrate compound (M/$\beta$-CyD=$\frac{1}{3}$) of this invention; and FIG. 2 is a diagram showing the concentrations of mobenzoxamine in blood over a given period of time when the clathrate compound of mobenzoxamine and $\beta$-cyclodextrin (M-$\beta$-CyD) of this invention was orally administered to beagles.

It has already been known to achieve the stabilization of pharmaceutically-effective unstable compounds by converting them to clathrate compounds with cyclodextrin. It is however a surprising finding that the conversion of mobenzoxamine or its salt to the clathrate compound results in promotion to its absorption through the digestive tract.

As salts of mobenzoxamine, may be used for example its inorganic acid salts such as its hydrochloride and sulfate and its organic acid salts such as its succinate, maleate, citrate and tartrate.

Cyclodextrin may be any one of its $\alpha$-, $\beta$- and $\gamma$-isomers. The $\beta$-isomer is most preferred for its excellent ability in forming clathrate compounds. The ratio of mobenzoxamine or its salt to cyclodextrin may preferably range from 1:1 to 1:4 by molar ratio.

As a method for forming a clathrate compound between mobenzoxamine or a salt thereof and cyclodextrin, it may be possible for example to employ the saturated solution method, in which mobenzoxamine or its salt is added to a saturated aqueous solution of cyclodextrin, or the kneading method in which cyclodextrin and mobenzoxamine or its salt or alcohol solution are kneaded with a relatively small amount of water.

The invention will hereinafter be described by the following Examples.

EXAMPLE 1

(i) Saturated Solution Method

Heated to about 60° C. was 250 ml of a 0.02M solution of $\beta$-cyclodextrin ($\beta$-CyD) in water, followed by an addition of 0.5 g of mobenzoxamine (M) thereto. The resultant mixture was dispersed for 30 minutes by ultrasonic generator and shaker, and was then shaken at 25° C. for 3 days on a rotary shaker. A white precipitate, which had deposited, was collected by filtration and was then dried to obtain 3.6 g of a clathrate compound (M/$\beta$-CyD=$\frac{1}{3}$). Its differential thermal analysis diagram is shown in FIG. 1.

(ii) Kneading Method (1)

Mobenzoxamine M was dissolved in methanol, followed by an addition of $\beta$-cyclodextrin ($\beta$-CyD) and a further addition of purified water thereto. After kneading the resultant mixture for 3 hours in a ball mill, the mixture was dried to obtain the following clathrate compounds.

| Clathrate compound (M/$\beta$-CyD) | 1/1 | $\frac{1}{2}$ | $\frac{1}{3}$ | $\frac{1}{4}$ |
|---|---|---|---|---|
| M (g) | 4 | 4 | 4 | 4 |
| $\beta$-CyD (g) | 10.36 | 20.72 | 31.08 | 41.44 |
| Methanol (ml) | 10 | 10 | 10 | 10 |
| Purified water (ml) | 20 | 30 | 40 | 50 |
| Yield (g) | 12.51 | 22.45 | 32.52 | 41.38 |

EXAMPLE 2

Mobenzoxamine dimaleate (M') was added to $\beta$-cyclodextrin ($\beta$-CyD), followed by an addition of purified water. The resultant mixture was kneaded for 3 hours in a ball mill, following by its drying to obtain the following compounds.

| Clathrate compound (M'/$\beta$-CyD) | 1/1 | 1/2 | 1/3 |
|---|---|---|---|
| M' (g) | 6 | 6 | 6 |
| $\beta$-CyD (g) | 10.55 | 21.1 | 31.65 |
| Purified water (ml) | 30 | 40 | 50 |
| Yield (g) | 14.95 | 24.90 | 34.81 |

EXAMPLE 3

The below-described samples, which had been prepared following the procedure of Example 1, and mobenzoxamine were respectively placed in flasks, each, to an amount equivalent to 50 mg in terms of mobenzoxamine, to each of which 50 ml of First fluid of the Japan Pharmacopoeia* was added. While maintaining their contents at 37° C., the amounts of remaining mobenzoxamine were measured over a given period of time. Experimental results are shown in Table 1.

*First fluid: Dissolve 2.0 g of sodium chloride in 24.0 ml of dilute hydrochloric acid and add sufficient water to make 1000 ml. This solution is colorless and clear, and its pH is about 1.2.

TABLE 1

| Sample | A | B | C | D | E |
|---|---|---|---|---|---|
| 0 hour | 100 | 100 | 100 | 100 | 100 |
| 1 hour | 95 | 94 | 92 | 85 | 60 |
| 2 hours | 88 | 88 | 81 | 72 | 39 |
| 4 hours | 80 | 78 | 69 | 50 | 17 |
| 6 hours | 70 | 68 | 57 | 36 | 10 |
| 8 hours | 62 | 62 | 47 | 24 | 2 |

Sample A: M/β-CyD (Sat'd Sol'n Method) = ⅓
Sample B: M/β-CyD (Kneading Method) = ⅓
Sample C: M/β-CyD (Kneading Method) = ½
Sample D: M/β-CyD (Kneading Method) = 1/1
Sample E: M

EXAMPLE 4

The below-described samples which had been prepared in accordance with the procedure of Example 1 were respectively stored at 60° C. and 80° C. and under humidified conditions (40° C./75% R.H.). The amounts of remaining M and changes in their external appearance were investigated over a given period of time. Investigation results are summarized in Table 2 and Table 3.

TABLE 2

| Sample | 1 | 2 | 3 | 4 | 5 | 6 | 7 |
|---|---|---|---|---|---|---|---|
| 0 day | 100 | 100 | 100 | 100 | 100 | 100 | 100 |
| 30 day | | | | | | | |
| 60° C. | 100 | 100 | 100 | 95 | 92 | 84 | 69 |
| 80° C. | 100 | 100 | 100 | 80 | 72 | 47 | 40 |
| Humidified | 100 | 100 | 100 | 97 | 95 | 90 | 88 |
| 60 day | | | | | | | |
| 60° C. | 100 | 100 | 100 | 90 | 73 | 67 | 55 |
| 80° C. | 100 | 100 | 100 | 75 | 59 | 34 | 21 |
| Humidified | 100 | 100 | 100 | 91 | 88 | 80 | 72 |

Sample 1: M/β-CyD (Sat'd Sol'n Method) = ⅓
Sample 2: M/β-CyD (Kneading Method) = 1/3.5
Sample 3: M/β-CyD (Kneading Method) = ⅓
Sample 4: M/β-CyD (Kneading Method) = 1/2.5
Sample 5: M/β-CyD (Kneading Method) = ½
Sample 6: M/β-CyD (Kneading Method) = 1/1
Sample 7: M

TABLE 3

Changes in Appearance (Degree of Whiteness)

| Sample | 1 | 2 | 3 | 4 | 5 | 6 | 7 |
|---|---|---|---|---|---|---|---|
| 0 day | 96 | 93 | 94 | 92 | 93 | 91 | 90 |
| 30 day | | | | | | | |
| 60° C. | 95 | 92 | 95 | 89 | 72 | 64 | 50 |
| 80° C. | 94 | 92 | 92 | 77 | 54 | 37 | 35 |
| Humidified | 95 | 91 | 93 | 91 | 85 | 75 | 56 |
| 60 day | | | | | | | |
| 60° C. | 95 | 92 | 94 | 87 | 71 | 60 | 35 |
| 80° C. | 94 | 92 | 92 | 68 | 42 | 27 | 25 |
| Humidified | 94 | 91 | 93 | 89 | 83 | 74 | 41 |

EXAMPLE 5

Using three beagles, the clathrate compound of this invention (M/β-CyD=⅓) and M were respectively and orally administered at 4.75 mg/kg in accordance with the crossover experiment method. Its concentration in blood were measured over a given period of time. Measurement results are shown in FIG. 2, in which the concentrations in blood were each indicated by the average value of the three beagles.

We claim:

1. An orally administratable mobenzoxamine complex comprising a clathrate compound of mobenzoxamine or a salt thereof and cyclodextrin, wherein the ratio of mobenzoxamine or the salt thereof to cyclodextrin ranges from 1:1 to 1:4 by molar ratio.

* * * * *